United States Patent [19]

Pavletic

[11] Patent Number: 5,649,960

[45] Date of Patent: Jul. 22, 1997

[54] APPARATUS AND METHOD FOR ACCELERATING THE STRETCHING OF SKIN

[76] Inventor: Michael M. Pavletic, 242 Pond St., Hopkinton, Mass. 01748

[21] Appl. No.: 383,255

[22] Filed: Feb. 3, 1995

[51] Int. Cl.$^6$ .................................................. A61B 17/08
[52] U.S. Cl. ........................... 606/216; 606/215; 606/218
[58] Field of Search ............................. 606/213, 215–218

[56] References Cited

U.S. PATENT DOCUMENTS

| | | | |
|---|---|---|---|
| 114,750 | 5/1871 | Battersby | 606/215 |
| 363,538 | 5/1887 | Penny | 606/215 |
| 2,421,193 | 5/1947 | Gardner | 128/335 |
| 3,402,716 | 9/1968 | Baxter | 128/335 |
| 3,559,652 | 2/1971 | Banitt | 128/334 |
| 4,646,731 | 3/1987 | Brower | 128/156 |
| 4,742,826 | 5/1988 | McLong | 606/215 |
| 4,825,866 | 5/1989 | Pierce | 128/335 |
| 5,234,462 | 8/1993 | Pavletic | 606/215 |
| 5,507,775 | 4/1996 | Ger et al. | 606/216 |

FOREIGN PATENT DOCUMENTS 2268504  11/1975  France.

OTHER PUBLICATIONS

Ling et al., "Presuturing—A New Technique for Closing Large Skin Defects: Clinical and Experimental Studies," *Plastic and Reconstructive Surgery*, 81(5):694–702 (1988).
Galil et al., "Effect of N–Butyl–2–Cyanoacrylate (Histoacryl Blue) on the Healing of Skin Wounds," *J. Canad. Dent. Assn.*, 7:565–569 (1984).
Mustoe et al., "Physical, Biomechanical, Histologic, and Biochemical Effects of Rapid Versus Conventional Tissue Expansion," *Plastic and Reconstructive Surgery*, 83(4):687–691 (1989).
Chedomir Radovan, "Tissue Expansion in Soft–Tissue Reconstruction," *Plastic and Reconstructive Surgery*, 74(4):482–490 (1984).
T. Gibson et al., "The Mobile Micro–Architecture of Dermal Collagen," *Brit. J. Surg.*, 52(10):764–770 (1965).
Gibson et al., "Directional Variation in Extensibility of Human Skin In Vivo", *J. Biomechanics*, 2:201–204 (1969).
Stark et al., "Directional Variations in Extensibility of Human Skin," *Brit. J. Plastic Surg.*, 30:105–114 (1977).
Hirshowitz et al., "A Skin–Stretching Device for the Harnessing of the Viscoelastic Properties of Skin," *Plastic and Reconstructive Surgery*, 92(2):260–270 (1993).

*Primary Examiner*—Michael Buiz
*Assistant Examiner*—Mark S. Leonardo
*Attorney, Agent, or Firm*—Hamilton, Brook, Smith & Reynolds, P.C.

[57] ABSTRACT

An apparatus and method are disclosed for accelerating the stretching of skin and the closing of open skin wounds. The method includes attaching a plurality of anchors to skin to allow a cable to be attached across the open skin wound. The cable is attached between the plurality of anchors across the wound, whereby when the skin stretches proximate to the wound sufficient tension is applied to the cable by an adjustable tightening mechanism member. Sufficient tension is applied to the cable by tightening mechanism member, whereby the skin proximate to said open skin would is stretched. The tension applied to the cable is detected and adjusted, as needed, to maintain the sufficient tension, thereby accelerating wound closure.

16 Claims, 3 Drawing Sheets

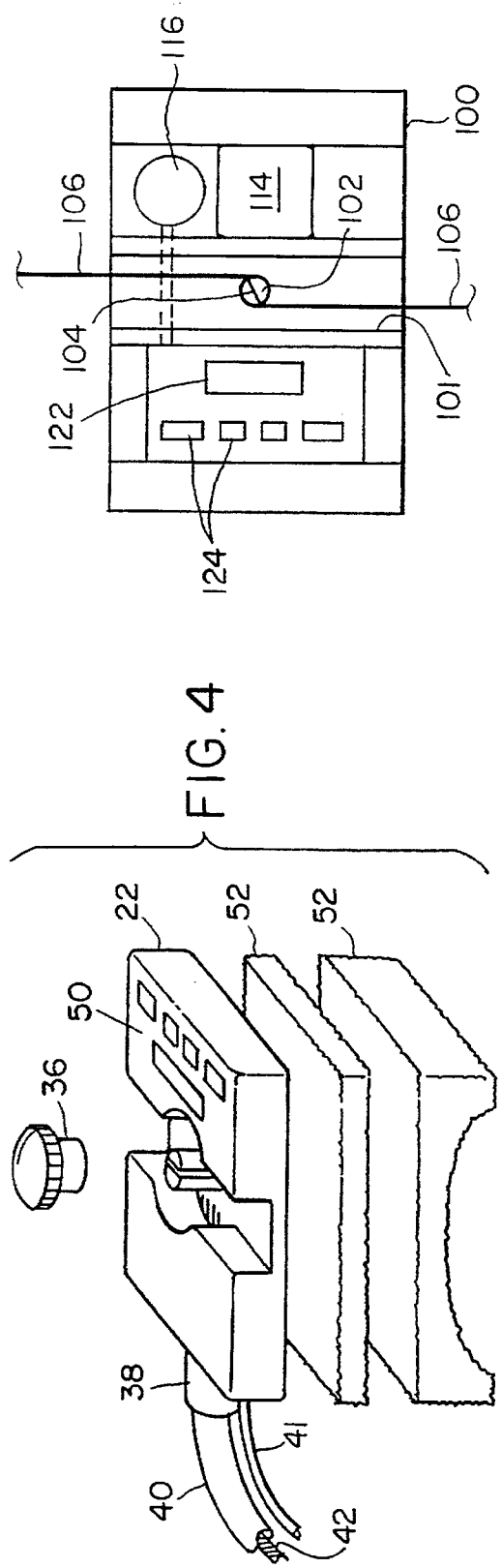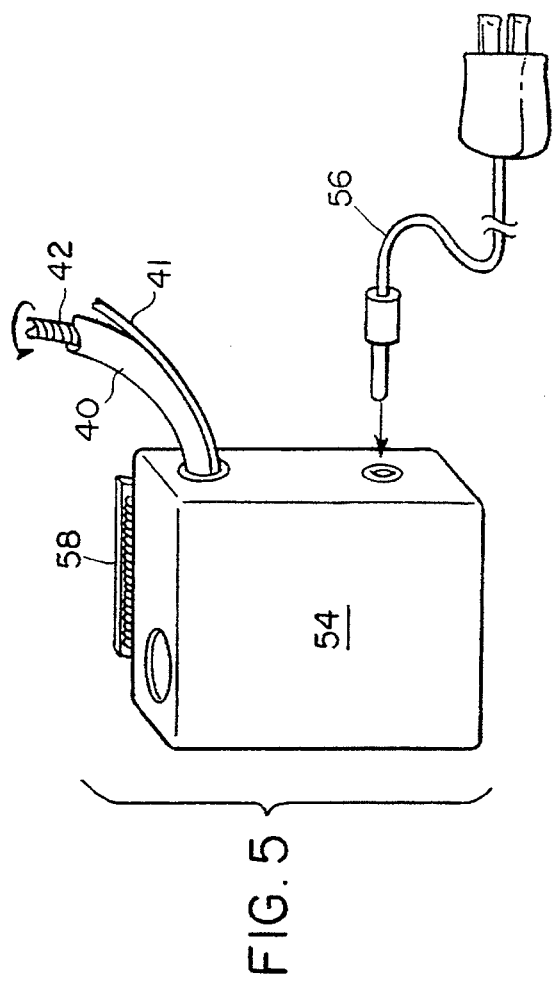

5,649,960

1

APPARATUS AND METHOD FOR ACCELERATING THE STRETCHING OF SKIN

BACKGROUND OF THE INVENTION

After skin has been wounded or burned, the opening must be closed to speed wound healing. In the cases of severe wounds or burns, there is insufficient excess skin around the sides of the defect to allow the sides to be pulled together. Similarly, when diseased or blemished cutaneous tissue is removed by surgery, insufficient skin may be left around the perimeter of the removed tissue. In the event the defect is large and cannot be easily closed, techniques have been developed for wound closure.

Two surgical techniques are skin grafts and skin flaps, both of which require the elevation of skin. Skin is incised and elevated from an area near the defect or from another part of the body. This invasive surgical procedure requires anesthesia, has substantial costs and requires hospitalization. Rigid asepsis is necessary. Further, there is the risk of complications which include skin ischemia and necrosis, infection, seroma and hematoma.

Another technique is the use of skin expanders. Skin expanders are implanted under the skin and slowly inflated to expand the skin. This technique is expensive. After gradual inflation of the expander, a second surgical procedure is required to rotate or advance the skin in the form of a flap. It requires surgical implantation, anesthesia, and hospitalization. As with skin grafts, rigid asepsis is necessary. The risk of complications include infection, implant extrusion, ischemia, necrosis, scar encapsulation of the silastic implant, hematoma and/or seroma formation.

A fourth technique is presuturing where the neighboring skin is folded temporarily over the proposed surgical site with sutures prior to the surgery, to facilitate wound closure as the skin relaxes to the tension applied by the sutures. Presuturing is minimally invasive because only placement of the suture needle is required prior to the elective surgical procedure. Local anesthesia is required for suture placement. The sutures are tightened but no adjustment is possible once the sutures have been placed in the skin. The sutures can be uncomfortable. There is a small risk of infection and the sutures have a limited surface area of application for closing open wounds.

A fifth and more recently developed technique, disclosed in U.S. Pat. No. 5,234,462, issued to Pavletic on Aug. 10, 1993, is a method which includes attaching a plurality of anchors to the surface of the skin adjacent to the wound with an adhesive. At least one elastomeric strap is positioned across the wound and is attached to the anchors. The tension of the elastomeric strap is adjusted periodically to maintain sufficient tension to progressively stretch the skin proximate to the fasteners over time.

SUMMARY OF THE INVENTION

The present invention relates to an improved apparatus and method for accelerating the stretching of skin and the closing of open skin wounds which includes the steps of attaching a plurality of anchors to skin to allow a cable to be attached across the open skin wound. The cable is attached between the plurality of anchors across the wound, whereby the skin stretches proximate to the wound when sufficient tension is applied to the cable by tension applying means. Sufficient tension is applied to the cable by tension applying means, whereby the skin proximate to the open skin is stretched. The tension applied to the cable is detected, and the tension is adjusted, as needed, to maintain the sufficient tension, thereby accelerating wound closure.

An apparatus for accelerating the stretching of skin and the closing of open skin wounds includes a plurality of anchors for attaching to skin to allow a cable to be attached across an area of skin to be stretched. The device further includes the cable for attaching at least two anchors. The device also includes tension applying means, whereby a tension can be applied to the cable which is sufficient to cause proximate skin to stretch. Means for detecting applied tension to the cable and for adjusting the tension, as needed, is for maintaining the sufficient tension.

This invention has many advantages. The method improves the rate of open skin wound healing by applying a tension to the skin, while not being invasive and not requiring anesthesia. The method can be used prior to an elective surgical procedure such as skin tumor removal, scar removal and removal of redundant skin, by mobilizing and stretching regional skin thereby facilitating skin closure after the surgery. The invention reduces tension on a surgical incision after closure. There is minimal pain to the patient during application and use. The straps, which hold the bandages over the wound, can be easily coupled and uncoupled for changing the bandages and wound assessment.

BRIEF DESCRIPTION OF THE DRAWINGS

FIG. 4 is another perspective view of the tension applying means shown in FIG. 1A.

FIG. 5 is a perspective view of the power supply as shown in FIG. 1.

FIG. 6 is a plan view of a second embodiment of the tension applying means of FIG. 1.

DETAILED DESCRIPTION OF THE INVENTION

The features and other details of the method and apparatus of the invention will now be more particularly described with reference to the accompanying drawings and pointed out in the claims. The same numeral present in different figures represents the same item. It will be understood that the particular embodiments of the invention are shown by way of illustration and not as limitations of the invention. The principal features of this invention can be employed in various embodiments without departing from the scope of the invention.

Figure 1:
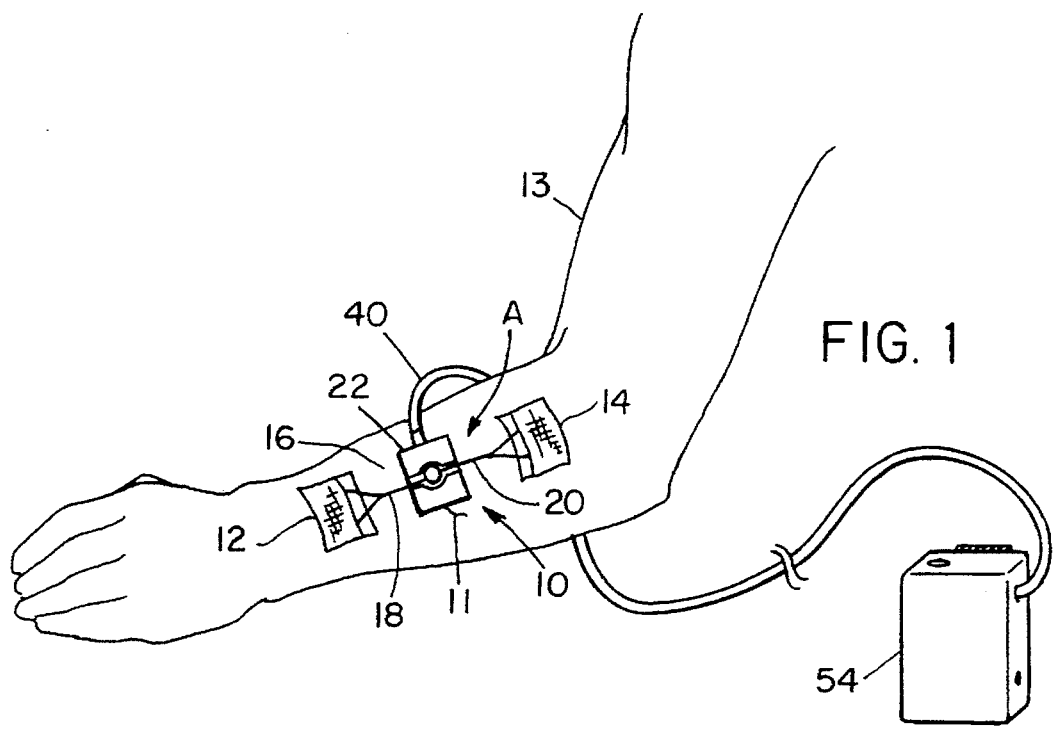
FIG. 1 is a perspective view of one embodiment of the elements of this invention.

In one illustration of the invention, shown in FIG. 1, elements 10 for accelerating the closing of open skin wound 11 on arm 13 include anchors 12,14. Anchors 12,14 can be made of suitable material that can bond to an adhesive. An example of a suitable material is a synthetic fiber woven into a fabric. In a preferred embodiment, the anchors are made of nylon. Anchors 12,14 can be of many shapes and sizes. A suitable shape and size are ones that sufficiently allow the anchors to bond with an adhesive or by another anchoring means to the skin 16 and withstand lateral tension from a cord. In one embodiment, the anchors are rectangular in shape with a length of about two inches and a width of about one inch. Alternatively, anchors 12,14 can be surgically attached to the skin by suturing or attached by some other means known in the art.

Skin 16, which is a non-injured section of the dermis, is adjacent to open skin wound 11. Open skin wound 11 is to be closed on the surface of the dermis. The wound can be a cut, a burn, a surgical incision or another opening in the dermis that necessitates closure. Alternatively, the skin can be an area that is to be prestretched prior to surgery to allow closure of a defect caused by surgical excision of the skin. Prestretching is used to prepare skin for closing after surgery for removing diseased or blemished cutaneous tissue such as a skin tumor or scar. Wrinkled and redundant skin for cosmetic removal during plastic surgery can be prestretched. Also, tendons, ligaments, etc. can be stretched by suturing the anchors to the connective tissue.

Skin 16 is suitably prepared for attaching anchors 12,14 by removing loose particles from the surface of the skin. An example of a suitable method includes cleaning the skin with soap and water or an alcohol.

If an adhesive is used, hair should be removed from the skin where the anchors are to be attached by a suitable method, such as by shaving. Particularly, the hair should be removed if it is thick. The thickness of the hair impairs the effectiveness with which an adhesive will bond the anchor to the skin. For animals with fur, such as dogs, the fur should be removed.

Anchors 12,14 can be attached to skin 16 with an adhesive or can be sutured. A suitable adhesive can sufficiently bond the anchors to the skin. In one embodiment, a suitable adhesive is a cyanoacrylate. In a particularly preferred embodiment, the adhesive is ethyl cyanoacrylate.

A suitable amount of the adhesive is placed on anchors 12,14 for bonding to the skin. In one embodiment, an anchor with an area of two square inches requires five or six drops of ethyl cyanoacrylate spaced over the anchors. Fifteen drops is usually equal to about one milliliter. The adhesive is applied by a suitable means, such as by squeezing droplets of the adhesive from a tube.

The adhesive is distributed over the surface of anchors 12,14 to have sufficiently even distribution of adhesive to allow bonding to a significant portion to the skin. Examples of a sufficiently even distribution of adhesive by which the anchors are bonded include drops, an array of drops, and a film spread over the bottom surface of the anchor prior to application to the skin.

The adhesive is allowed to set. Typically, cyanoacrylates set quickly upon contact with air. In one embodiment, the ethyl cyanoacrylate sets within seconds of exposure to the air.

Cords 18,20 are attached to anchors 12,14, respectively. Cords 18,20 are connected by various means such as snaps, clasp, and hook and eyelets. Alternatively, cord 18,20 can be sutured into the skin directly to act as both the anchor and cord. Cords are made of a suitable material that is able to withstand the tension necessary to stretch skin in order to accelerate the closing of an open skin wound. A suitable strap can be of a material that is either compressive or non-compressive. In one embodiment, the straps are rubber bands or bungee cords. Cords are made of a suitable size and shape. Cords have lengths that are sufficient to cross the wound. The thickness and widths of the cords are sufficient to withstand the tension applied.

Figure 2:
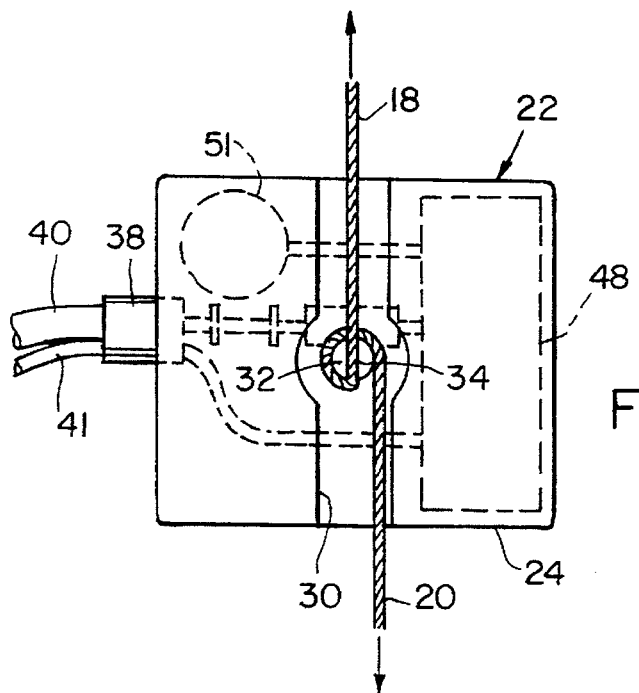
FIG. 2 is a plan view of the tension applying means shown in Detail A in FIG. 1.
Figure 3:
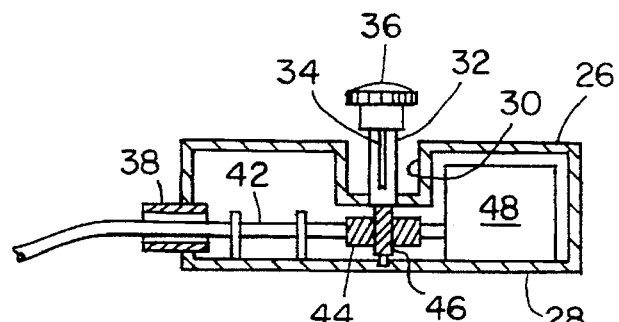
FIG. 3 is a cross-sectional view of the tension applying means shown in FIG. 1A.

Located midway between anchors 12,14 on cords 18,20 is tightening means 22, which is shown in Detail A in FIG. 1 and in greater detail in FIG. 2 from an overview and in FIG. 3 from a side view. Tightening means 22 has housing 24, which has top side 26 and bottom side 28. Slot 30 crosses top side 28 of housing 24, which is for orienting cords 18,20. Shaft 32 in slot 30 is for tightening cords 18,20 by rotation. Shaft 32 has shaft slot 34 which is sufficiently sized to allow cords 18,20 to slip into shaft slot 34. Shaft 32 can rotate in order to gather up a portion of cord, thereby tightening cords 18,20. Cap 36 is placed on shaft 32 for holding cords 18,20 in shaft slot 34 and can allow an operator to rotate shaft 32. Housing 24 has cable connector 38 for receiving cable housing 40 and cable shaft 42 for powering tightening means 22. Signal wire 41 is attached to the exterior of cable housing 40 for relaying signal from tightening means 22 to activate a low-speed motor when tension decreases as a result of skin stretching.

Inside tightening means 22, as shown in FIG. 3, cable connector 38 is connected to cable shaft 42, which has worm wheel 44 on cable shaft 42, which is coupled to worm gear 46 on shaft 32. Cable shaft 42 allows shaft 32 to rotate, thereby tightening cords 18,20 to maintain tension as needed. Also, included in housing 24 is tension sensor 48. An example of a suitable tension sensor, which can be powered by lithium battery 51 or other suitable power source, is a microchip tension sensor that can be preset to a desired tension. Tension sensor 48 is connected to worm wheel 44 for sensing torque and tension from worm gear 46 on shaft 34. Tension sensor 48 is also connected by signal wire 41 to motor power source 54, shown in FIG. 5.

A perspective view of housing 22 is shown in FIG. 4. On top side 26 of housing is digital display 50 which can be preset to desired tension and display the tension. Housing 22 on bottom side 28 can have pads 52 of various shapes and sizes to fit body contours. Pads 52 can be replaceable foam pads with an adhesive surface that adheres to bottom side 28 of tightening means 22 and patient's skin bandage/dressing overlying a wound/lesion or, alternatively, to housing 22 only. Pads 52 are made of a suitable rubber, plastic foam or cloth material. Contoured adherent pads 52 can be removed and replaced on the housing.

Motor power source 54, shown in FIG. 5, is employed to provide power to tightening means 22 to continuously and automatically maintain tension on cords 18,20 by rotating cable shaft 42, which causes shaft 32 to rotate. Motor power source 54 can be powered by a suitable means, such as a battery or by electrical cord 56. Tightening means 22 can be controlled by tension sensor 48 employed to monitor a decrease in cable tension at shaft 32 on tightening means 22. Tension sensor 48 operates in conjunction with an electrical motor in motor power source 54. Tension sensor 48 detects a decrease in torque at shaft 32, thereby determining a decrease in cable tension. A signal is sent through signal wire 41 from housing 22 to a relay switch that activates a low-speed motor in motor power source 54 when tension drops as the result of skin relaxation. Rotary cable 42 rotates within cable housing 40 in response to rotation from the motor to restore the predetermined tension at shaft 32. Motor power source 54 for the electrical motor can be from a self-contained battery or a separately attached battery power pack. The electrical motor can also be incorporated into the power pack connected to the automatic stretching device by cable shaft 42 in cable housing 40, which can rotate shaft 32, thereby tightening cords 18,20. Alternatively, the timing mechanism may be in the form of a conventional egg timer style mechanism that can tighten cords 18,20 at about the rate skin can stretch. Motor power source 54 can be secured to the patient or patient's garments by spring-loaded clip 58 attached to the exterior power source 54.

Figure 7:
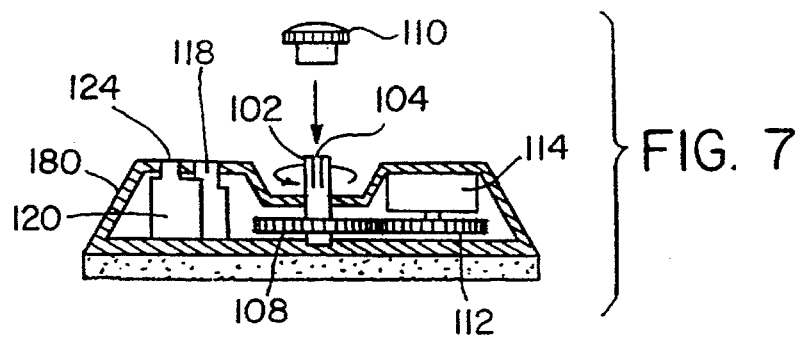
FIG. 7 is a cross-sectional view of the second embodiment shown in FIG. 2A.
Figure 8:
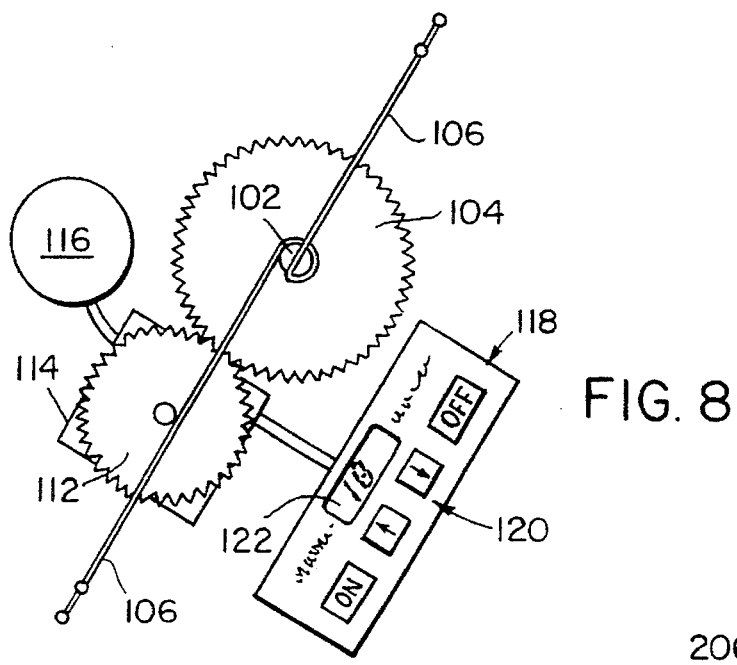
FIG. 8 is a schematic plan view of the second embodiment shown in FIG. 2A without the housing.

A second embodiment of tightening means is shown in FIG. 6, a top view, in FIG. 7, a side view, and in FIG. 8, a schematic plan view. Housing 100 has groove 101 for maintaining orientation of cord 106. Cable spindle 102, which has slot 104 for receiving cord 106, is attached to spindle gear 108. Cable spindle 102 has cap 110 for holding cable 106 in slot 104. Cable spindle 102 is coupled to motor gear 112 for driving spindle cable 102, whereby cable 106 can be tightened. Motor gear 112 is attached to motor 114, which can be electrically powered by battery 116, such as a lithium battery. Housing 100 also has sensing means 118, such as a microchip, for sensing tension on cable 106 at cable spindle 102. Sensing means 118 has means for adjusting tension 120 and tension window display 124.

Figure 9:
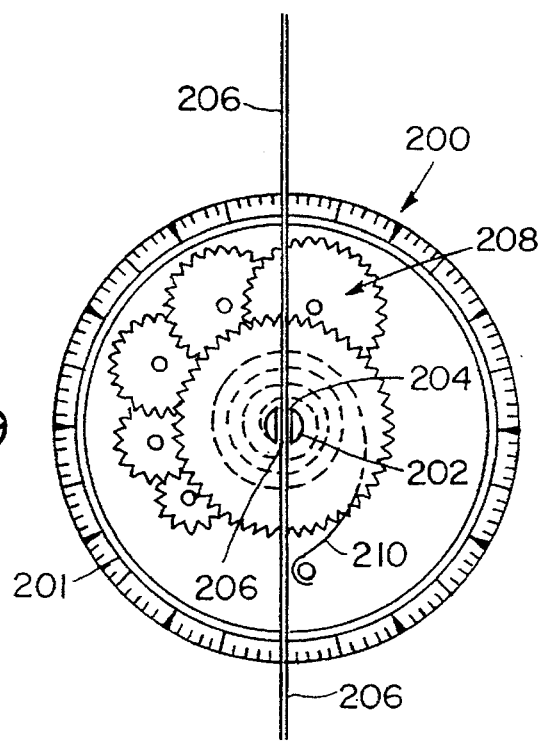
FIG. 9 is a cross-sectional plan view of a third embodiment of tension applying means.

In a third embodiment, as shown in a cross-sectional plan view in FIG. 9, tightening means is gear and spring "egg timer" mechanism 200 having housing 201. Gear mechanism 200 has shaft 202 and shaft slot 204 on housing 201 for cord 206 insertion. Gears 208 are connected to spring means 210, such as a spring coil, whereby shaft 202 is rotated at a regular interval by spring means 210, thereby maintaining a continuous tension on cord 206. Gear mechanism 200 can be set for various amounts of time, such as 48 hours or greater, before being rewound.

Returning to FIG. 1, Anchors 12,14 are attached to skin 16 proximate to open skin wound 11. Cords 18,20 are attached between anchors 12,14 across open skin wound 11. An appropriate tension is set on tightening means 22 which is sufficient to stretch the skin proximate to open skin wound 11 by progressive mobilization of skin by the process of mechanical creep and stress relaxation. The appropriate tension can be established based on empirical measurements of skin advancement in millimeters over a time sequence at specific tensions for the different types of tissue to be stretched, human, canine, etc. The selected tension is applied by rotating shaft 32 to cause tension to be applied through tightening means 22 cords 18,20 to anchors 12,14. Tension is maintained essentially constant during stretching by tightening means 22. The skin proximate to open skin wound is stretched, thereby accelerating wound closure or skin stretching.

Equivalents

Those skilled in the art will recognize, or be able to ascertain using no more than routine experimentation, many equivalents to the specific embodiments of the invention described specifically herein. Such equivalents are intended to be encompassed in the scope of the claims.

What is claimed is:

1. A method for accelerating the stretching of skin and the closing of open skin wounds, comprising the steps of:
   a) attaching a plurality of anchors to skin to allow a cable to be attached across the open skin wound;
   b) attaching the cable between the plurality of anchors across the wound, whereby the skin stretches proximate to the wound when sufficient tension is applied to the cable by a tension applying means;
   c) applying sufficient tension that is essentially constant to the cable by tension applying means, whereby the skin proximate to said open skin wound is stretched; and
   d) detecting the tension applied to the cable and adjusting the tension to maintain the sufficient tension essentially constant during stretching, thereby accelerating wound closure.

2. The method of claim 1 wherein the anchors are attached by sutures.

3. The method of claim 1 wherein the anchors are attached by an adhesive.

4. The method of claim 1 wherein the tension applied by the tension applying means is selectable.

5. An apparatus for stretching skin, comprising:
   a) a cable having at least two anchors for attaching to skin to allow the cable to be attached across an area of skin to be stretched;
   b) tension applying means attached to said cable, whereby a tension can be applied to the cable which is sufficient to cause skin proximate to said anchors to stretch; and
   c) means for detecting applied tension to the cable and for adjusting the tension, as needed, to maintain the sufficient tension essentially constant, said means for detecting being attached to said cable.

6. The apparatus of claim 5 wherein tension applying means is electrically powered.

7. The apparatus of claim 4 wherein the tension applying means can be a tension that is selectable.

8. The apparatus of claim 6 wherein tension applying means is electrically powered by a battery.

9. The apparatus of claim 6 wherein tension applying means is powered by a spring and gear mechanism.

10. The apparatus of claim 6 wherein the cables are compressive.

11. The apparatus of claim 6 wherein the cables are non-compressive.

12. An apparatus for stretching skin, comprising:
   a) a cable having at least two anchors for attaching to skin with an adhesive, to allow the cable to be attached across an area of skin to be stretched; and
   b) a spring and gear mechanism for applying tension, said mechanism being attached to said cable, whereby a tension can be applied to the cable, which is sufficient to cause skin proximate to said anchors to stretch while the tension is adjusted to maintain sufficient tension essentially constant.

13. A method for accelerating the stretching of tissue, comprising the steps of:
   a) attaching a plurality of anchors with an adhesive to tissue to allow a cable to be attached across the tissue to be stretched;
   b) attaching the cable between the plurality of anchors, whereby when sufficient tension is applied to the cable by a tension applying means the tissue stretches proximate to the anchors;
   c) applying sufficient tension to the cable by constant tension applying means, whereby the tissue proximate to the anchors is stretched; and
   d) detecting the tension applied to the cable and adjusting the tension, to maintain the sufficient tension essentially constant during stretching, thereby accelerating the stretching of tissue.

14. The method of claim 13 wherein the tissue includes ligaments.

15. The method of claim 13 wherein the tissue includes tendons.

16. A method for accelerating the stretching of tissue, comprising the steps of:
   a) attaching a plurality of anchors with an adhesive to tissue to allow a cable to be attached across the tissue to be stretched;
   b) attaching the cable between the plurality of anchors, whereby when sufficient tension is applied to the cable by a spring and gear mechanism the tissue stretches proximate to the anchors; and c) applying a constant tension to the cable by the spring and gear mechanism for applying tension, which is sufficient to stretch skin at an essentially constant rate proximate to said anchors, thereby accelerating the stretching of tissue.

* * * * *